United States Patent [19]

Vanderveen

[11] Patent Number: 5,171,301
[45] Date of Patent: Dec. 15, 1992

[54] MULTIPLE MINI-PUMP INFUSION SYSTEM

[75] Inventor: Timothy W. Vanderveen, Poway, Calif.

[73] Assignee: IMED Corporation, San Diego, Calif.

[21] Appl. No.: 776,580

[22] Filed: Oct. 15, 1991

[51] Int. Cl.$^5$ ............................................. A61M 5/00
[52] U.S. Cl. .................... 604/141; 604/83; 604/153
[58] Field of Search ............ 604/67, 141, 151, 153, 604/83; 128/DIG. 12, DIG. 13

[56] References Cited

U.S. PATENT DOCUMENTS

| | | | |
|---|---|---|---|
| 3,989,913 | 11/1976 | Lundquist et al. | 200/35 R |
| 4,270,532 | 6/1981 | Franetzki et al. | 128/213 R |
| 4,282,872 | 8/1981 | Franetzki et al. | 128/213 R |
| 4,308,866 | 1/1982 | Jelliffe et al. | 128/214 |
| 4,391,598 | 7/1983 | Thompson | 604/65 |
| 4,431,425 | 2/1984 | Thompson et al. | 604/246 |
| 4,457,750 | 7/1984 | Hill | 604/65 |
| 4,464,172 | 8/1984 | Lichtenstein | 604/65 |
| 4,469,481 | 9/1984 | Kobayashi | 604/67 |
| 4,475,901 | 10/1984 | Kraegen et al. | 604/67 |
| 4,487,604 | 12/1984 | Iwatschenko et al. | 604/153 |
| 4,496,351 | 1/1985 | Hillel et al. | 604/250 |
| 4,498,843 | 2/1985 | Schneider et al. | 417/22 |
| 4,526,515 | 7/1985 | DeVries | 604/153 |
| 4,553,958 | 11/1985 | LeCocq | 604/67 |
| 4,624,661 | 11/1986 | Arimond | 604/151 |
| 4,634,430 | 1/1987 | Polaschegg | 604/141 |
| 4,657,490 | 4/1987 | Abbott | 417/478 |
| 4,662,829 | 5/1987 | Nehring | 604/153 |
| 4,692,145 | 9/1987 | Weyant | 604/65 |
| 4,696,671 | 9/1987 | Epstein et al. | 604/67 |
| 4,705,506 | 11/1987 | Archibald | 604/67 |
| 4,712,590 | 12/1987 | Gianflippo | 604/153 |
| 4,714,462 | 12/1987 | DiDomenico | 604/141 |
| 4,756,706 | 7/1988 | Kerns et al. | D8/DIG. 13 |
| 4,785,799 | 11/1988 | Schoon et al. | 128/53 |
| 4,874,359 | 10/1989 | White et al. | 128/DIG. 12 |
| 4,886,431 | 12/1989 | Soderquist et al. | 604/153 |
| 4,921,480 | 5/1990 | Sealfon | 604/67 |
| 4,950,245 | 8/1990 | Brown et al. | 604/67 |
| 5,090,963 | 2/1992 | Gross et al. | 604/141 |
| 5,100,380 | 3/1992 | Epstein | 128/DIG. 13 |

OTHER PUBLICATIONS

Fleming, Richard C. et al. *Home Parenteral Nutrition as Primary Therapy in Patients which Extensive Crohn's Disease of the Small Owel and Malnutrition.* The American Gastroenterological Association, vol. 73, No. 5, 1977, pp. 1077-1081.

Matuchansky, et al. *Cyclic (Nocturnal) Total Parenteral Nutrition in Hospitalized Adult Patients with Severe Digestive Diseases.* Gastroenterology, 1981, vol. 81, 1981, pp. 433-437.

Messing, B., M.D., et al. *Metabolic Study During Cyclic Total Parenteral Nutrition in Adult Patients with and without Corticosteroid-induced Hypercatabolism: Comparison with Standard Total Parenteral Nutrition.* Journal of Parenteral and Enteral Nutrition, vol. 7, No. 1, 1983, pp. 21-25.

Page, Carey P. M.D. *Man the Meal Eater and His Interaction with Parenteral Nutrition.* JAMA, vol. 244, No. 17, 1980, pp. 1950-1953.

Travacare Home Therapy. *HomePro: A New Era in Nutritional Support.* Bulletin 5, 1986.

*Primary Examiner*—Paul J. Hirsch
*Attorney, Agent, or Firm*—Nydegger & Associates

[57] ABSTRACT

An apparatus for infusing multiple fluid medicaments to a patient includes a base for supporting a plurality of pumping chambers. Each pumping chamber has a housing and a flexible membrane attached to the housing to establish a contractible fluid chamber between the housing and the membrane for holding a fluid medicament. Separate IV lines extend in fluid communication from each of the pumping chambers and each line is individually engageable with a flow controller which is mounted on the base. An electronic controller is mounted on the base and is operatively connected with each of the flow controllers to individually open each IV line at a predetermined time, and for a predetermined period of time, to establish a sequence for infusing fluids to the patient from the separate pumping chambers.

18 Claims, 3 Drawing Sheets

MULTIPLE MINI-PUMP INFUSION SYSTEM

FIELD OF THE INVENTION

The present invention pertains to IV administration sets which are useful for infusing fluid medicaments to a patient. More particularly, the present invention pertains to administration sets which are capable of infusing a plurality of fluids to a patient from a plurality of different IV fluid sources using individual pumping apparatus. The present invention is particularly, but not exclusively, useful for the timed initiation and sequencing of various IV infusions from a plurality of IV fluid sources in accordance with a prescribed protocol.

BACKGROUND OF THE INVENTION

Intravenous (IV) administration sets which are useful for infusing medical fluids to a patient are well known and widely used. In the most simple configuration, an IV administration set includes a fluid source, an IV line connecting the fluid source to the patient, and a medical device operatively associated with the IV line to influence the rate of fluid flow to the patient. Not surprisingly, several medical devices have been proposed for this purpose.

Typically, medical devices which are used in IV administration sets are generally categorized as either pumps or controllers. The difference between the two being that controllers rely on gravity for the flow of fluid through the set, while pumps exert a mechanical force on the fluid to establish a fluid flow. Within the pump category, several different types can be identified. For example, one type of pump which is frequently used in an IV administration set is a volumetric pump. A volumetric pump incorporates a valved fluid chamber in combination with a reciprocal piston such as is disclosed in U.S. Pat. No. 3,985,133 which is assigned to the same assignee as the present invention. Another type of pump which can be used in an IV administration set is a peristaltic pump. Quite different from the volumetric pump, the peristaltic pump creates a moving zone of occlusion along the IV line and uses this action to pump fluid through the administration set. An example of this type pump is disclosed in U.S. Pat. No. 4,617,014 which is also assigned to the same assignee as the present invention. Further, there are mechanisms which do not act in association with the IV line between the fluid source and the patient. Instead, mechanisms of this type act directly on the fluid source to pump fluid from the source and through the set to the patient. Such a mechanism is disclosed in U.S. Pat. No. 4,544,369 and is an example of the familiar syringe pump. Still another type device for administering medical fluids to a patient incorporates both the fluid source and the pumping mechanism into a self-contained combination. As an example, such a device can rely on the contraction of an elastomeric membrane to provide the forces necessary to pump fluid from the device. A device of this type is disclosed in U.S. Pat. No. 4,968,301 which is assigned to the same assignee as the present invention. It is a device of this latter type that is of importance for the present invention.

With advancements in medicine, and the development of complex medical procedures and protocols to implement these advancements, there has been increased reliance on infusion therapy for the care and maintenance of patients. Not infrequently, infusion therapy requires the concerted administration of several fluid medicaments in a prescribed timed sequence. To do this, IV administration set systems that incorporate multiple fluid sources and multiple pumping mechanisms need to be assembled. Unfortunately, the assembly and implementation of such a system is inherently complex and somewhat cumbersome. Consequently, the more simple the system can be, the better.

One simplification for a multiple medicament IV infusion system is to use fewer components. Thus, a self-contained device which combines both the fluid source and the pumping mechanism in a single unit may be preferred. A single unit which uses an elastomeric membrane for its pumping mechanism also has other benefits. The fact such a device is not electrically operated, and the fact it can be pre-loaded with a predetermined amount of fluid medicament, both simplify its use. Further, the pumping mechanism itself has no power requirements and needs no complicated electrical hook-up. A single such device, however, can not implement a multiple medication protocol. Accordingly, there is a need for a system which coordinates the concerted use of multiple pumps of this type.

In light of the above it is an object of the present invention to provide a multiple medicament system for infusing IV fluids to a patient which uses a plurality of self-contained units that each have their own fluid source and pumping mechanism. Another object of the present invention is to provide a multiple medicament system for infusing IV fluids to a patient which coordinates the time duration and sequencing for infusion of a plurality of independent IV administration sets. Still another object of the present invention is to provide a multiple medicament system for infusing IV fluids to a patient which is modular in order to accommodate different numbers of IV administration sets. Yet another object of the present invention is to provide a multiple medicament system for infusing IV fluids to a patient which is simple to use, relatively easy to manufacture and comparatively cost effective.

SUMMARY OF THE INVENTION

In accordance with the present invention, a multiple medicament system for infusing IV fluids to a patient includes a base formed with a plurality of supports. Additionally, a plurality of IV line occluders are mounted on the base and each occluder is positioned for associated use with a respective support.

As intended for the present invention, the supports on the base are each formed to receive an individual pumping chamber. Specifically, each pumping chamber comprises a plate or housing and a flexible membrane which is attached to the housing to establish a contractible fluid chamber between the housing and the membrane. Additionally, the housing of each pumping chamber has a fluid port which provides a fluid pathway into the fluid chamber. To fill the pumping chamber with medical fluid, the desired amount of fluid medicament is injected through the port and into the fluid chamber. A standard syringe can be used for this purpose. Importantly, as this fluid is injected into the chamber, the membrane is stretched to establish a potential force for subsequent pumping of the fluid from the chamber.

A separate IV fluid line is attached to the exit port of each pumping chamber and, with the pumping chamber positioned in a support on the base, the IV line is operatively engaged with an occluder. Downstream from the occluder, the IV line is connected in fluid communication with other IV lines from other pumping chambers or, alternatively, can be connected directly to the patient.

The multiple medicament system of the present invention also includes a command console mounted on the base and a microprocessor, also mounted on the base, which electronically interconnects the command console with the occluders. Specifically, the command console includes tactile switches for programming the microprocessor and a visual display to indicate the program which is established by the operator. In accordance with programmed instructions, the microprocessor operates individual occluders to open their associated IV line to permit infusion of fluid from the connected pumping chamber and through the particular IV line to the patient. Accordingly, the operation of individual IV administration sets can be controlled both as to the time of initiation of their operation and the duration of their operation. Further, throttle and valve controls can be used and controlled by the microprocessor to perform prescribed infusion protocols. Still further, the membranes can be designed to provide different infusion pressures for sequencing the various fluids to the infused. In this manner the multiple medicament system of the present invention is able to establish a timed sequence for the overall operation of the system.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
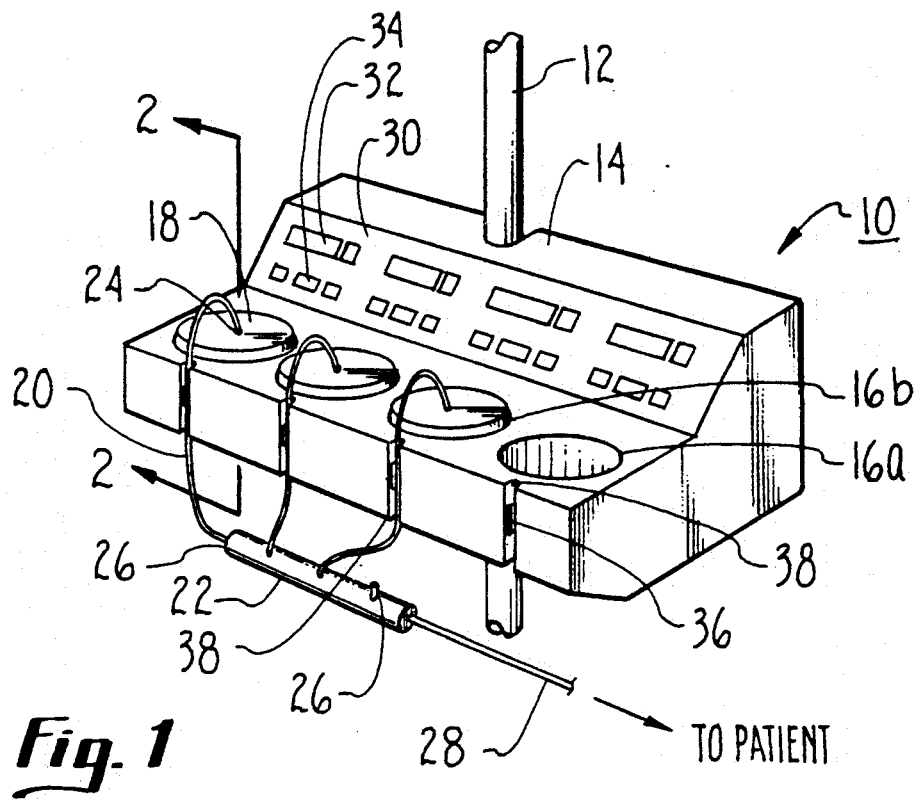
FIG. 1 is a perspective view of the multiple medicament infusing system.

Referring initially to FIG. 1 the apparatus for the multiple medicament infusing system of the present invention is shown assembled and generally designated 10. For use in the environment of a hospital or a medical facility, the apparatus 10 can be mounted on an IV pole 12 or some similar type structure to facilitate its use. As shown, the apparatus 10 includes a base 14 which is formed with a plurality of supports 16 of which the supports 16a and 16b are representative. Preferably, the supports 16 are receptacles which are located on the front of the apparatus 10 and which are shaped to individually receive and hold a pumping chamber 18.

The fluid flow path for each of the individual IV administration sets that are included in the system of the present invention begins at a pumping chamber 18. An IV tube 20 (also referred to as an IV line) is connected in fluid communication between the pumping chamber 18 and a multi-port connector 22. More specifically, one end of the IV line 20 is connected in fluid communication with the pumping chamber 18 through a port connecter 24 which is part of the pumping chamber 18. The other end of IV line 20 is connected in fluid communication with the multi-port connector 22 through one of the adapters 26 which are formed on the connector 24. The multi-port connector 22 is then connected in fluid communication with a patient (not shown) through the IV line 28.

FIG. 1 also shows that the base 14 of apparatus 10 has a control console 30 on which are mounted a plurality of visual displays 32 and a plurality of tactile push buttons 34. Further, the base 14 is formed with a plurality of slots 36 and a plurality of flow controllers or occluders 38 which are mounted on the base 14 for operative association with a respective slot 36. While the present invention discloses primarily apparatus for occluders 38 it is to be appreciated that other fluid flow controlling devices (not shown) can also be used within the spirit of the present invention. In any event, as intended for the present invention, each pumping chamber 18 and the IV line 20 with which it is connected, together establish a separate IV administration set. The flow of fluid through each such IV administration set to the patient is then coordinated and sequenced with the other IV administration sets in the system by the apparatus 10. Specifically, each IV line 20 is positioned in a particular slot 36 for selective occlusion by the occluder 38 associated with the particular slot 36. The occluder 38, in turn, is controlled in accordance with instructions which are programmed into the apparatus 110 from the control console 30.

Figure 2:
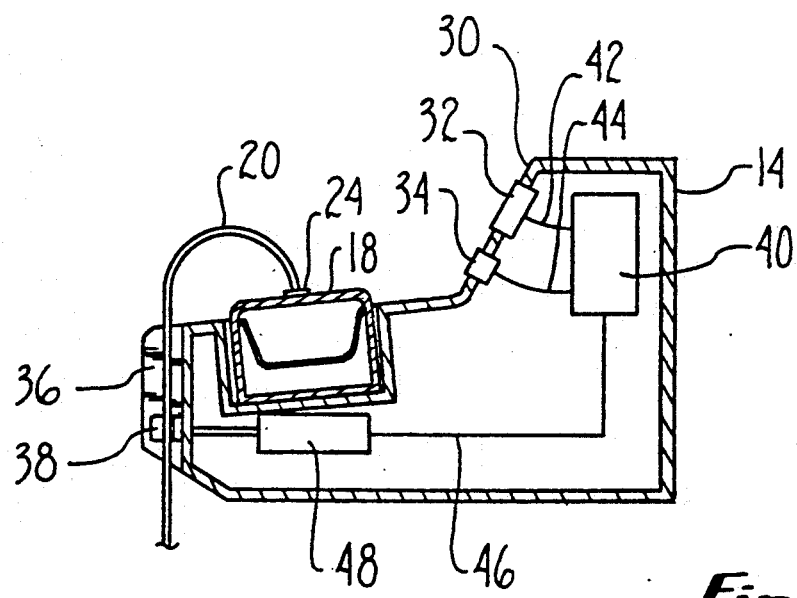
FIG. 2 is a cross sectional view of the multiple medicament infusing system as seen along the line 2—2 in FIG. 1 with selected components shown schematically for clarity.

In FIG. 2 it will be seen that the apparatus 10 includes a microprocessor 40 which is mounted inside the base 14 in a manner well known in the pertinent art. FIG. 2 also shows that the microprocessor 40 is electrically connected to the visual display 32 on control console 30 via the electrical line 42 and electrically connected to the tactile push buttons 34 on control console 30 via the electrical line 44. Further, microprocessor 40 is electrically connected to an occluder 48 via an electrical line 46. Importantly, each tactile push button 34, each corresponding visual display 32, and each corresponding occluder mechanism 48 together comprise a control unit, and each such control unit operates separately through the microprocessor 40 to independently control a single IV administration set. The microprocessor 40, however, is capable of coordinating the operation of a plurality of control units and their respective IV administration sets and to sequence their infusion of medical solutions to the patient in accordance with a predetermined program.

Figure 3:
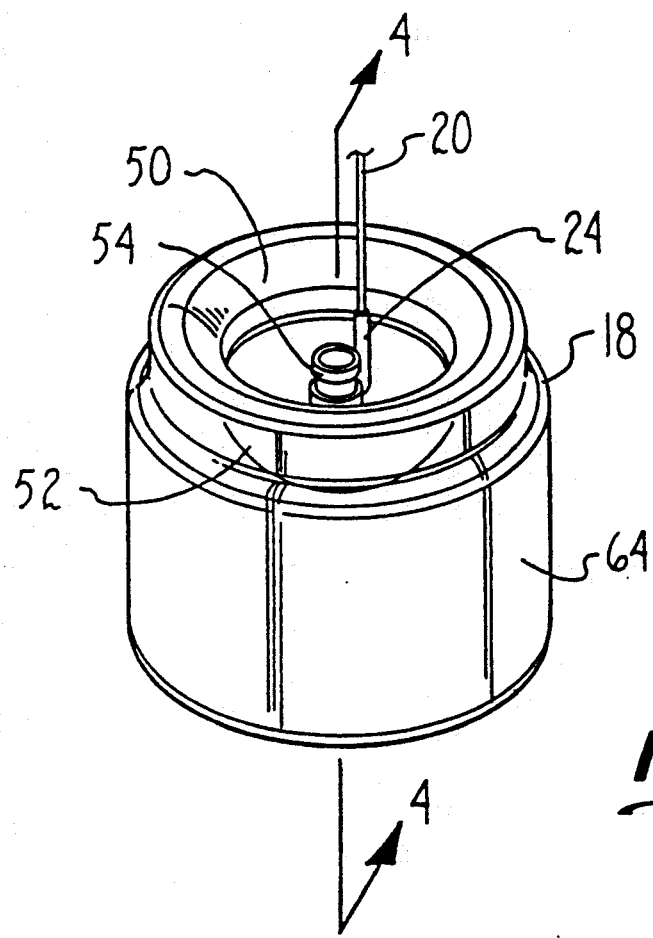
FIG. 3 is a perspective view of the preferred embodiment of the pumping unit for the present invention.

The preferred embodiment of the pumping chamber 18 for the apparatus 10 of the present invention is shown in FIG. 3. There it will be seen that the chamber 18 includes a housing 50 which is made of a relatively rigid material, such as polyvinyl chloride, polyurethane or polyethelene or the like. The housing 50 is generally dome-shaped and, as shown, can be substantially hemispherical. An inlet port 54 with a one-way valve assembly 56 is established as part of the housing 50.

A ring assembly 58 supports an elastomeric membrane 60, and the ring assembly 58 is attached to the periphery of the housing 50. With this attachment the membrane 60 is stretched across and over the contour surface 52. As intended for the present invention, the initial placement of membrane 60 over contour surface 52 stretches the membrane 60 into its nonlinear region of elasticity. Furthermore, as will be appreciated by the person of ordinary skill in the art, the membrane 60 will remain in this nonlinear region of elasticity as the membrane 60 is subjected to additional stretching during the operation of the apparatus 10. More specifically, as fluid medicament is introduced or pumped through the inlet port 54, by any suitable means such as a syringe pump (not shown), the fluid medicament will stretch the membrane 60 to create a fluid chamber 62. During this additional stretching, the membrane 60 remains stretched into its nonlinear region of elasticity.

Figure 4:
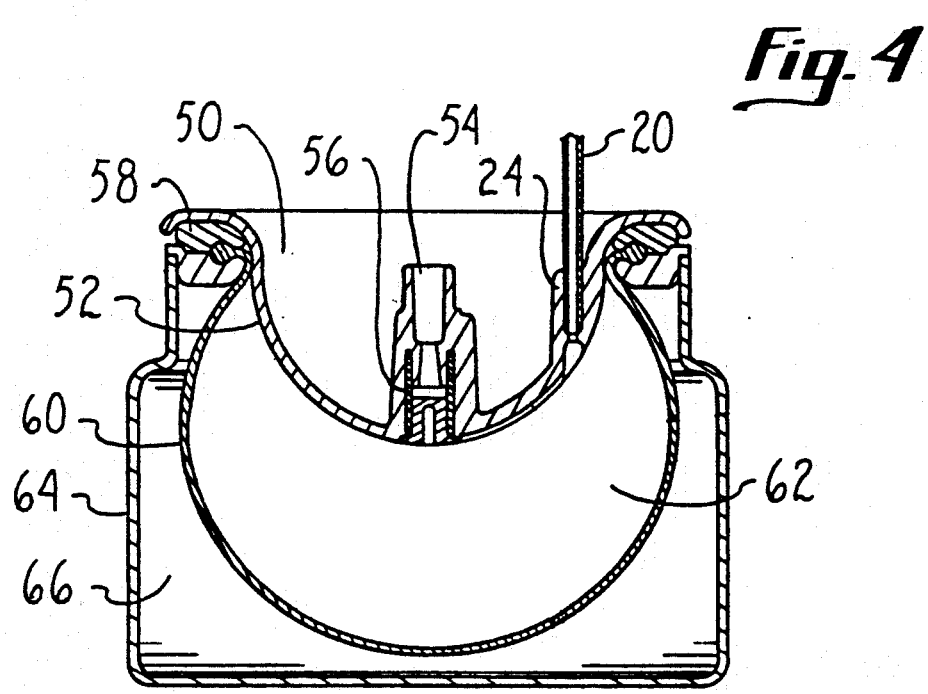
FIG. 4 is a cross-sectional view of the preferred embodiment of the pumping unit of the present invention as seen along the line 4—4 in FIG. 3.

As best seen in FIG. 4, the expanding/contracting fluid chamber 62 is created between the membrane 60 and the contour surface 52 of housing 50. For all stretched configurations of the membrane 60, and FIG. 4 shows but one such configuration, the membrane 60 remains in its nonlinear region of elasticity. As recognized by the present invention, during the contraction of the membrane 60 from a position, such as shown in FIG. 4, to the position wherein the membrane 60 is collapsed onto the contour surface 52, the membrane 60 will create a substantially constant fluid pressure within the collapsing fluid chamber 62. This is due to the fact that membrane 60 remains in its nonlinear region of elasticity during this contraction. Consequently, with this substantially constant fluid pressure in the fluid chamber 62, flow control through the IV tube can be more easily controlled by the occluder 38 (flow controller).

Both FIG. 3 and FIG. 4 shown that the pumping chamber 18 also includes a shell 64 which is attached to the ring assembly 58 to surround the housing 50 and the membrane 60. The shell 64 can be dimensioned to be received into a support 16 on the base 14. Additionally, the shell 64 establishes cavity 66 into which the membrane 60 can expand as the fluid chamber 62 is being filled with fluid medicament.

Figure 5:
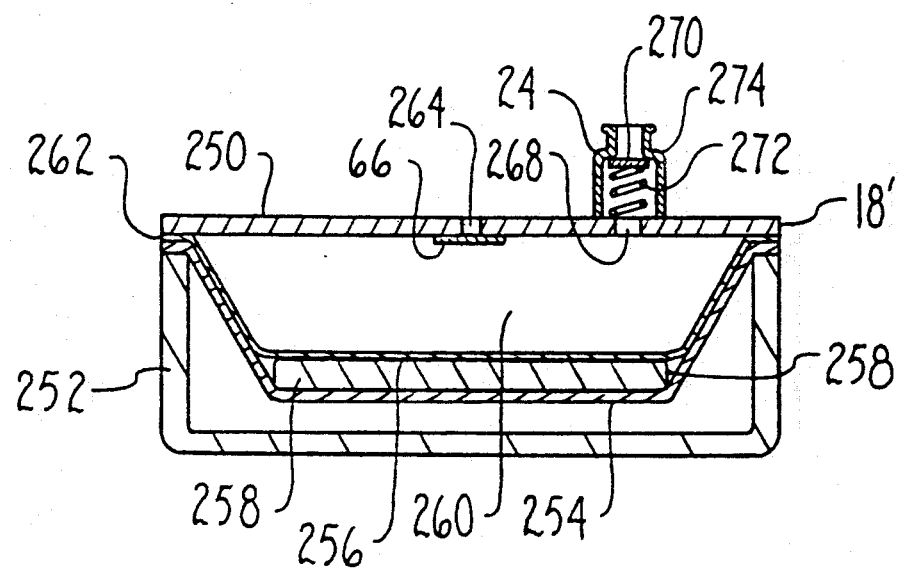
FIG. 5 is a detailed cross sectional view of an alternate embodiment of the pumping chamber of the present invention as seen in FIG. 2.

An alternate embodiment for a pumping chamber which is usable within apparatus 10 is shown in FIG. 5. There it will be seen that a pumping chamber 18' includes a plate 250 which covers a cup shaped housing 252. A stretchable membrane 254 and a liner 256 enclose an impeller plate 258 and, together, create an expandable and contractible fluid chamber 260 between the liner 256 and the plate 250. As shown, the stretchable membrane 254 and the liner 256 are attached between the plate 250 and the housing 252 at the juncture 262 between the liner 256 and the housing 252. For purposes of the present invention, the stretchable membrane 254 can be made of any suitable elastomeric material which will urge the impeller plate 258 toward and into contact with the plate 250. Also, it is to be appreciated that, with some design modifications, the impeller plate 258 can be eliminated and only the membrane 254 used to create a pumping force on the fluid. Further, liner 256 can be made of any suitable material which is chemically and biologically compatible with the fluid medicament to be introduced into the chamber 260. The size of the impeller plate 258 can vary to some degree, but it should be sufficiently large to maintain some stretch in membrane 254 and keep the force from membrane 254 on impeller plate 258 relatively constant, even when the chamber 260 has been completely collapsed.

FIG. 5 also shows that the plate 250 of pumping chamber 18' is formed with an air vent 264 which is covered by a hydrophobic layer 66. Accordingly, when chamber 260 is filled with fluid, air in the chamber 260 can escape through air vent 264 without also loosing fluid from the chamber 260. Plate 250 of pumping chamber 18' is also formed with a fluid port 268 which is surrounded by the port connector 24. A valve 270 is located between the plate 250 and the port connector 24 which is urged by a spring 272 against the shoulder 274 of port connector 24. With this combination, fluid can be injected into the chamber 260 while valve 270 is depressed and, after chamber 260 has been filled, valve 270 will prevent pumping of fluid from the chamber 260 until port connector 24 is appropriately connected with a fluid line 20. It will be appreciated that various valving arrangements for fluid chamber 260 will suffice for purposes of the present invention.

Figure 6:
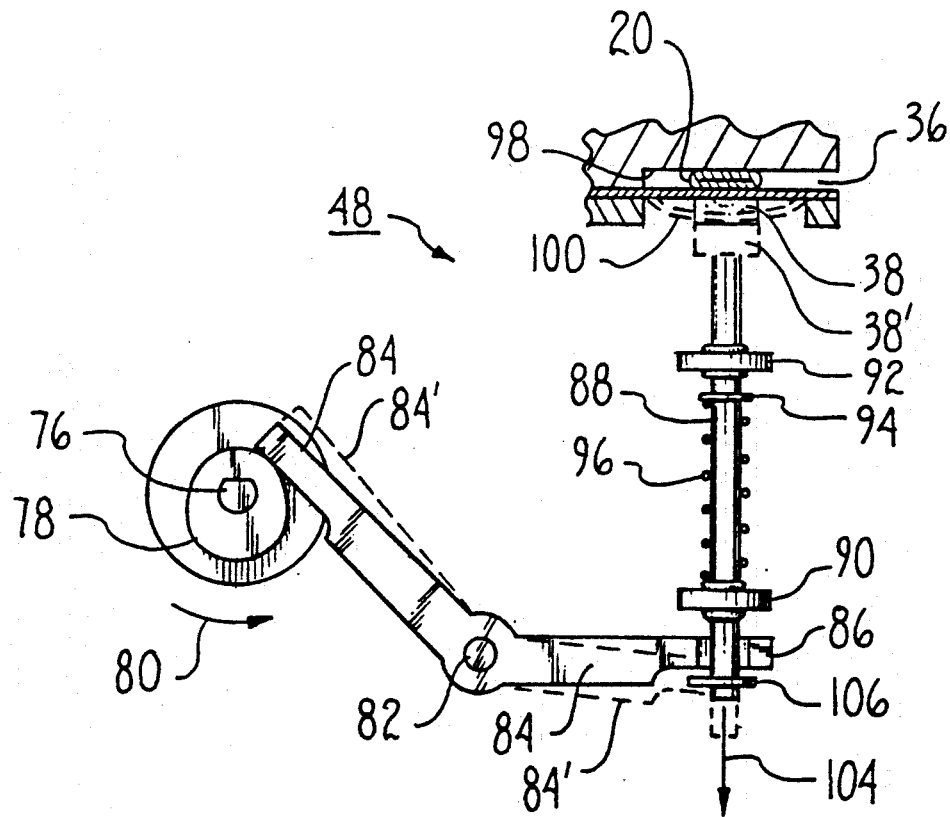
FIG. 6 is a top plan view of an embodiment for an occluder for the present invention shown in operative association with an IV line.

The occluder mechanism 48 is shown in FIG. 6 to include a drive shaft 76 which is mounted on the base 14 for rotation by a motor (not shown). A cam 78 is fixedly attached to the drive shaft 76 for rotation with the drive shaft in the direction indicated by arrow 80. A pivot pin 82 is also mounted on base 114 and an actuator arm 84 is attached to the pin 82. Consequently, as cam 78 is rotated to urge against the actuator arm 84, the actuator arm 84 will pivot about the rotational axis of the pivot pin 82. An end 86 of actuator arm 84 is operatively engaged with a shaft 88 for operation of the occluder mechanism 48. Specifically, a bearing 90 and a bearing 92 are each mounted on the base 14 and the shaft 88 is slidably mounted on the bearings 90,92. Further, the shaft 88 is formed with a retainer ring 94 and a spring 96 is positioned around the shaft 88 between the retainer ring 94 and the bearing 90. The occluder 38 of occluder mechanism 48 is mounted on the end of shaft 88 as shown and will reciprocate with the movement of shaft 88. FIG. 6 also shows that the slot 36 creates a platen 98 and includes a flexible cover 100. As intended for the present invention, IV tube 20 is positioned in the slot 36 between the platen 98 and the flexible cover 1100. As shown, the occluder 38 is positioned against flexible cover 100 on the side of cover 100 opposite IV tube 20. With this structure, a rotation of drive shaft 76 urges cam 78 against arm 84 to pivot the arm 84 around pivot pin 82 and into the position shown for arm 84'. As a result, end 86 of arm 84 urges against the abutment 102 on shaft 88 to move shaft 88 in the direction of arrow 104 and against the action of spring 96. Consequently, occluder 38 moves into the position shown for occluder 38' and the IV tube 20 positioned in slot 36 will be opened for fluid flow. Further, rotation of the shaft 76 will release shaft 88 from the influence of actuator arm 84 and allow spring 96 to urge occluder 38 into contact with tube 20 to prevent fluid flow through the IV tube 20.

OPERATION

In the operation of the multiple medicament system of the present invention, the operator first positions the base 14 on the IV pole 14. A pumping chamber 18 is then selected and the pumping chamber is filled with a medicament to be infused. Specifically, a syringe or some other device for pumping fluid is attached to the port connector 24 and fluid is injected into the fluid chamber 62 of pumping chamber 18. As fluid is so injected the membrane 60 is distanced from the housing 50 and chamber 62 expands under the influence of the injected medicament to stretch the membrane 60. During the filling of pumping chamber 18 any air in chamber 60 is initially vented through the IV tube 20. The result is that chamber 62 is filled only with the medicament to be infused. As will be appreciated by the skilled artisan, several pumping chambers 18 can be prefilled and stored before use. Further, each individual chamber 18 is filled with a particular medicament which can be different from the medicaments used to fill other pumping chambers 18. Further, each pumping chamber 18 can be prefilled at a remote site, e.g. the pharmacy of the hospital, and individually transported to the location where the medicament is to be infused to the patient.

Each filled pumping chamber 18 is connected in fluid communication with an IV tube 20 by attaching one end of the tube 20 to the port connector 24. The pumping chamber 18 is then positioned in a support 16 on base 14 and a portion of the IV tube 20 which extends from the pumping chamber 18 is positioned in a slot 36 for operative contact with an occluder mechanism 48 associated with the particular slot 36. The free end of tube 20 can then be attached to a multi-port connector 22 which directs fluid infused through the tube 20 to the patient. Importantly, upon placement of the tube 20 in slot 36 and into contact with an occluder mechanism 48, the occluder mechanism 48 initially occludes the tube 20.

The microprocessor 40 of base 14 is programmed by the operator using tactile push buttons 34 on control console 30. According to this program, the occluder mechanism 48 of the particular occluder 38 will be activated to open tube 20 at a preselected time and for a predetermined duration. Similarly, the other pumping chambers 18 can be filled and operatively mounted on the base 14. Consequently, base 14 can control the initiation and duration of infusion from a plurality of pumping mechanisms 18. In this way, the system provides a procedure for the timed sequencing of a plurality of prefilled pumping chambers 18.

It is also to be understood that the microprocessor 40 can be set to control the rate of infusion from each of the pumping chambers 18. To do so, the apparatus 10 will incorporate throttling or valving devices (not shown) which are connected with the microprocessor 40 and which are operable to control the rate of fluid flow through the lines 20 from the respective pumping chambers 18. Consequently, the apparatus 10 is useable with a plurality of individually portable, self-contained pumping chambers 18 which can be collectively controlled to accomplish a prescribed infusion protocol.

In all important respects the operation for the preferred embodiment for the pumping chamber 18 (FIG. 31) is similar to the alternate embodiment for the pumping chamber 18' (FIG. 5). The materials for the corresponding structure are similar. More importantly, however, is the fact that the apparatus 10 for the present invention can function with either embodiment of the pumping chamber 18 or with their substantial equivalents.

While the particular multiple medicament system for infusing IV fluids to a patient as herein shown and disclosed in detail is fully capable of obtaining the objects and providing the advantages herein before stated, it is to be understood that it is merely illustrative of the presently preferred embodiments of the invention and that no limitations are intended to the details of the construction or design, herein shown other than as defined in the appended claims.

I claim:
1. A multiple medicament system for infusing IV fluids to a patient which comprises:
   a base;
   a plurality of flow controllers mounted on said base;
   a plurality of individual pumping chambers, each of said pumping chambers comprising:
      a housing having a fluid port, said housing being formed with a surface having a periphery and a predetermined contour circumscribed by said periphery; and
      an elastomeric membrane attached to said periphery over said contour surface to stretch said membrane into a nonlinear region of elasticity and create a potential chamber between said stretched membrane and said housing for receiving one of said fluids therein through said port and expelling said fluid therefrom through said port by nonlinear contraction of said membrane at a substantially constant pressure;
   a plurality of IV fluid lines, each said fluid line being attached in fluid communication with one of said fluid ports and operatively engaged with one of said flow controllers for transferring fluid medicament from said attached pumping chamber to the patient; and
   means mounted on said base and operatively connected with each of said flow controllers for sequencing fluid flow from said pumping chambers.

2. A system as recited in claim 1 wherein said predetermined contour is substantially hemispherical in shape.

3. A system as recited in claim 1 further comprising a plurality of supports formed on said base, each said support being positioned for receiving and holding one of said pumping chambers in operative association with one of said flow controllers.

4. A system as recited in claim wherein said sequencing means comprises means for timed sequencing of fluid flow through selected IV fluid lines.

5. A system as recited in claim 3 wherein said sequencing means is a microprocessor.

6. A multiple medicament system for infusing IV fluids to a patient which comprises:
   a base;
   a plurality of flow controllers mounted on said base;
   a plurality of individual pumping chambers wherein each said pumping chamber comprises a base plate and a flexible membrane attached to said base plate to establish a contractible fluid chamber therebetween for receiving one of said fluids therein through said port and expelling said fluid therefrom by nonlinear contraction of said membrane, each said pumping chamber further having an outlet for connecting said IV line in fluid communication with said fluid chamber;
   a plurality of IV fluid lines, each said fluid line being attached in fluid communication with one of said pumping chambers and operatively engaged with one of said flow controllers for transferring fluid medicament from said attached pumping chamber to the patient; and
   means mounted on said base and operatively connected with each of said flow controllers for sequencing fluid flow from said pumping chambers.

7. A system as recited in claim 6 wherein each said pumping chamber further comprises an inlet for injection a predetermined amount of medicament into said pumping chamber.

8. A system as recited in claim 5 wherein said sequencing means further comprises means for operating said flow controllers to open selected of said IV fluid lines for a predetermined period of time.

9. A multiple mini-pump fluid infusion system which comprises:
   a base formed with a plurality of supports;
   a plurality of occluder mechanisms mounted on said base, each said occluder mechanism being separately associated with one of said supports;
   a plurality of infusion pumps, each said pump having a housing, a flexible membrane attached to said housing to establish a contractible fluid chamber therebetween for holding fluid to be infused and expelling said fluid therefrom by nonlinear contraction of said membrane, each said pump further having an outlet in fluid communication with said fluid chamber;
   a plurality of fluid lines, each said line being connected in fluid communication with an outlet of one of said pumps and positioned to be occluder by one of said occluders; and
   programmable electronic means operatively connected with each said occluded for establishing fluid flow from each said pump through a respective said fluid line.

10. A system as recited in claim 9 wherein each said pump further comprises an inlet for injecting a predetermined amount of medicament into said contractible fluid chamber of said pump.

11. A system as recited in claim 9 wherein said programmable means comprises means for timed sequencing of fluid flow through selected IV fluid lines further comprises means for operating said occluders to open selected said fluid lines for a predetermined period of time.

12. A system as recited in claim 11 wherein said programmable means is a microprocessor.

13. A method for infusing a plurality of medical fluids to a patient which comprises the steps of:
   providing a fluid medicament infusion system comprising a base; a plurality of flow controllers mounted on said base; a plurality of individual pumping chambers each of which include a housing and a flexible membrane attached to said housing to establish a contractible fluid chamber therebetween for receiving one of said fluids therein through said port and expelling said fluid therefrom by nonlinear contraction of said membrane; a plurality of IV fluid lines, each said fluid line being attached in fluid communication with one of said pumping chambers and operatively engaged with one of said flow controllers for transferring fluid medicament from said attached pumping chamber to the patient; and means mounted on said base and operatively connected with each of said flow controllers for sequencing fluid flow from said pumping chambers;
   filling selected said pumping chambers with fluid to be infused to the patient; and
   opening said flow controllers in accordance with a predetermined sequence.

14. A method as recited in claim 13 further comprising the step of establishing a specific time for opening each said flow controller.

15. A method as recited in claim 13 further comprising the step of maintaining a selected said flow controller in an open configuration for fluid flow through said associated fluid line for a predetermined period of time.

16. A method as recited in claim 13 further comprising the step of providing a plurality of supports formed on said base, each said support being positioned for receiving and holding one of said pumping chambers in operative association with one of said flow controllers.

17. A method as recited in claim 13 wherein said pumping chambers of said system further comprise an outlet for connecting said IV line in fluid communication with said fluid chamber.

18. A method as recited in claim 13 wherein each said pumping chamber further comprises an inlet for injecting a predetermined amount of medicament into said pumping chamber.

* * * * *